United States Patent
Goedje et al.

(10) Patent No.: US 8,016,766 B2
(45) Date of Patent: Sep. 13, 2011

(54) CENTRAL VENOUS CATHETER ASSEMBLY FOR MEASURING PHYSIOLOGICAL DATA FOR CARDIAC OUTPUT DETERMINATION AND METHOD OF DETERMINING CARDIAC OUTPUT

(75) Inventors: Oliver Goedje, Deining (DE); Stephan Joeken, Loerrach (DE); Joerg Scheier, Munich (DE); Marcus Veeck, Koblenz (DE)

(73) Assignee: Pulsion Medical Systems AG, Munich (DE)

( * ) Notice: Subject to any disclaimer, the term of this patent is extended or adjusted under 35 U.S.C. 154(b) by 339 days.

(21) Appl. No.: 12/288,979

(22) Filed: Oct. 24, 2008

(65) Prior Publication Data

US 2009/0137917 A1    May 28, 2009

(30) Foreign Application Priority Data

Nov. 23, 2007   (EP) .................... 07121386

(51) Int. Cl.
*A61B 5/02*   (2006.01)
(52) U.S. Cl. ........................ 600/526; 606/505
(58) Field of Classification Search .......... 600/504–505, 600/508–527
See application file for complete search history.

(56) References Cited

U.S. PATENT DOCUMENTS

| | | | |
|---|---|---|---|
| 4,507,974 A | 4/1985 | Yelderman | |
| 4,841,981 A * | 6/1989 | Tanabe et al. | 600/505 |
| 5,174,299 A | 12/1992 | Nelson | |
| 5,217,019 A | 6/1993 | Hughes | |
| 5,509,424 A | 4/1996 | Al-Ali | |
| 5,526,817 A | 6/1996 | Pfeiffer et al. | |
| 5,701,908 A | 12/1997 | Carlson et al. | |
| 5,857,976 A | 1/1999 | Quinn et al. | |
| 6,939,307 B1 * | 9/2005 | Dunlop | 600/504 |
| 2003/0225336 A1 * | 12/2003 | Callister et al. | 600/505 |
| 2004/0181158 A1 | 9/2004 | Bowman | |
| 2006/0136023 A1 * | 6/2006 | Dobak | 607/105 |

FOREIGN PATENT DOCUMENTS

| | | |
|---|---|---|
| EP | 1 236 435 | 9/2002 |
| EP | 1 419 732 | 5/2004 |
| WO | WO 98/14114 | 4/1998 |
| WO | WO 01/13808 | 3/2001 |

* cited by examiner

*Primary Examiner* — Niketa Patel
*Assistant Examiner* — Catherine Vorrhees
(74) *Attorney, Agent, or Firm* — Collard & Roe, P.C.

(57) ABSTRACT

The central venous sensor assembly comprises a catheter body with several proximal ports. The catheter portion placed in the vena cava superior is equipped with a proximal flux measurement unit, and the catheter portion placed in the vena cava inferior is equipped with a distal flux measurement unit. A first input channel supplies a measurement signal indicative of a flux vp to the evaluation unit from which the latter calculates a blood flow in the vena cava superior. Likewise, a second input channel supplies a measurement signal indicative of a flux vd to the evaluation unit from which the latter calculates a blood flow rate in the vena cava inferior. Due to continuity, the sum of the flow rates in the upper and lower central veins corresponds to the flow rate through the right heart and in the pulmonary artery and thus to cardiac output.

22 Claims, 3 Drawing Sheets

CENTRAL VENOUS CATHETER ASSEMBLY FOR MEASURING PHYSIOLOGICAL DATA FOR CARDIAC OUTPUT DETERMINATION AND METHOD OF DETERMINING CARDIAC OUTPUT

BACKGROUND OF THE INVENTION

1. Field of the Invention

The present invention relates to a central venous catheter assembly for measuring physiological data for cardiac output determination. Further, the present invention also relates to a method of determining cardiac output.

It is well known and widely applied practice, in particular in the fields of critical and intensive care, to determine cardiac output of a patient from measurement data acquired using catheters and measurement equipment adapted thereto. Therein, various measurement techniques can be applied, which are either based on the principle of observing a dilution process upon inducing a disturbance to the circulatory system (thermodilution, indicator dilution or double dilution techniques) or on the principle of observing blood pressure variation over time and typically evaluating the blood pressure variation on the basis of a modified Windkessel model (pulse contour analysis techniques).

2. The Prior Art

Generally, two catheter application schemes are common. Either a right heart catheter is used, which extends into the pulmonary artery (pulmonary artery catheter), or an arterial catheter (e.g. in the arteria radialis) in combination with a central venous catheter (transpulmonary measurement setup). Increasingly, the latter arrangement is preferred for being less invasive, since application of balloon catheters to the right heart may in some cases lead to severe complications such as malignant arrythmias and pulmonary artery rupture or infarction. However, an even less invasive measurement setup would certainly be welcomed for facilitating clinical practice.

A large variety of invasive cardiac output determination techniques as briefly summarized above are known from a number of publications. In U.S. Pat. No. 5,526,817 a transpulmonary thermodilution setup is described, wherein a cold bolus is injected through a central venous catheter and the temperature response is measured using an arterial catheter. Instead of using cold bolus injections, heated pulmonary artery catheters are used for modified thermodilution methods such as described in U.S. Pat. Nos. 4,507,974 and 5,217,019. Periodic heat pulses at a given pattern are introduced substantially apart from the distal end of the catheter by a heating coil or a thermal filament mounted to the indwelling catheter. Temperature changes of the blood heated when passing the heating coil or thermal filament, respectively, are measured downstream by a thermistor at the distal end of the catheter. Cardiac output is determined quasi-continuously based on the data sampled for several minutes using signal processing and averaging algorithms. Approaches to regulate the heat transferred by the catheter are described in U.S. Pat. Nos. 5,701,908 and 5,857,976. To avoid the above described general risk of pulmonary artery catheters, EP 1 236 435 A1 suggests employing a heated central venous catheter and measuring the temperature response using an arterial catheter equipped with a temperature sensor (transpulmonary setup). EP 1 236 435 A1 further describes combining this technique with pulse contour methods based on arterial pressure readings.

As an alternative to heating blood for thermodilution measurements, it has also been suggested to detect the energy needed for keeping a heat transfer element arranged on a pulmonary arterial catheter at a constant temperature slightly above blood temperature, or, as a similar approach, to measure the resulting temperature of such a heat transfer element when slightly heated with a known supply of energy scheme. Therein, usually two temperature sensors are employed, a first temperature sensor measuring the temperature of the heat transfer element and a second temperature sensor spaced some distance away from the heat transfer element measuring the blood temperature. As higher flow velocities improve heat transfer, the power supplied to the heat transfer element to achieve a given resulting temperature above blood temperature is approximately proportional to flow velocity (depending on Reynolds number). Catheter systems functioning according to this general approach have been described in U.S. Pat. No. 5,509,424 and WO 01/13808 A1. As already mentioned, these systems are based on pulmonary arterial catheters, the application of which is linked with the above-described risks.

SUMMARY OF THE INVENTION

In view of this technical background, it is an object of the present invention to provide a further reduction of invasiveness in cardiac output determination without sacrificing accuracy.

According to one aspect of the present invention, this object is solved by providing a central venous catheter assembly for measuring physiological data for cardiac output determination, the measurement assembly comprising a distal intravascular portion for placement in the vena cava inferior of a patient and a proximal intravascular portion for placement in the vena cava superior of the patient, a distal flux measurement unit arranged in the distal intravascular portion and adapted to provide raw measurement data for determination of a blood flow in the direction towards the proximal intravascular portion, and a proximal flux measurement unit arranged in the proximal intravascular portion and adapted to provide raw measurement data for determination of a blood flow in the direction towards the distal intravascular portion. Preferred embodiments of the present invention may be configured with additional features.

According to another aspect of the present invention, the above object is achieved by a method for determining cardiac output of patient comprising receiving raw measurement data from a first flux measurement unit which measures flux-related raw measurement data in the vena cava inferior, receiving raw measurement data from a second flux measurement unit which measures flux-related raw measurement data in the vena superior, determining a first blood flow from the raw measurement data received from said first flux measurement unit, determining a second blood flow from the raw measurement data received from said second flux measurement unit, and determining the cardiac output as a sum of said first blood flow and said second blood flow. Preferred embodiments of the inventive method can be configured with additional features and/or steps.

The main concept of the present invention is providing for determining flow rate in both upper and lower central vein (vena cava superior and inferior). Due to continuity, the sum of the two thus determined flow rates equals the flow rate through the right heart, at least if averaged over a sufficient period of time.

This concept allows for a very low degree of invasiveness as neither a pulmonary artery catheter nor an arterial catheter are needed. However, it is also possible to combine the inventive concept with techniques known from the prior art, e.g. transpulmonary dilution techniques or pulse contour analysis techniques, in order to enhance functionality, improve accuracy and/or enable improved calibration schemes.

The measurement of the flow rates in the upper and lower central vein may be achieved using techniques which are per se known from the prior art, such as thermodilution based on local emission of heat pulses or continuous heating and observing the relation between energy input and resulting temperature. As an alternative, cooling Peltier elements may also be applied and either used for thermodilution measurements or observing the relation between energy input and resulting temperature.

The two flux measurement units do not necessarily need to be entirely independent but may also be constructed such that they share certain elements in some possible cases of implementation. For example, when implementing the technique of observing the relation between energy input and resulting temperature of the heat transfer element, according to the prior art usually two temperature sensors are employed, a first temperature sensor measuring the temperature of the heat transfer element and a second temperature sensor spaced some distance away from the heat transfer element measuring the blood temperature. When following this approach within the concept of the present invention employing two heat transfer elements, three temperature sensors may be sufficient, i.e. one for each heat transfer element and a third one for measuring the blood temperature in some distance away, e.g. between the two heat transfer elements.

It is to be understood that a central venous sensor assembly according to the present invention may be equipped for performing additional functions. For example, an applied catheter body may comprise a pressure measurement lumen, which may advantageously end proximal to both flux measurement units, distal to both measurement units or between them. Additional lumina for withdrawing samples or injecting substances may also be provided. The central venous sensor assembly may also serve as a carrier for optical measurement equipment, e.g. fiber-optical probes for measuring blood oxygen saturation.

Generally, any of the embodiments described or options mentioned herein may be particularly advantageous depending on the actual conditions of application. Further, features of one embodiment may be combined with features of another embodiment as well as features known per se from the prior art as far as technically possible and unless indicated otherwise.

BRIEF DESCRIPTION OF THE DRAWINGS

The invention will now be described in more detail. The accompanying drawings, which are schematic illustrations, serve for a better understanding of the features of the present invention. Therein

DETAILED DESCRIPTION OF THE PREFERRED EMBODIMENTS

Figure 1:
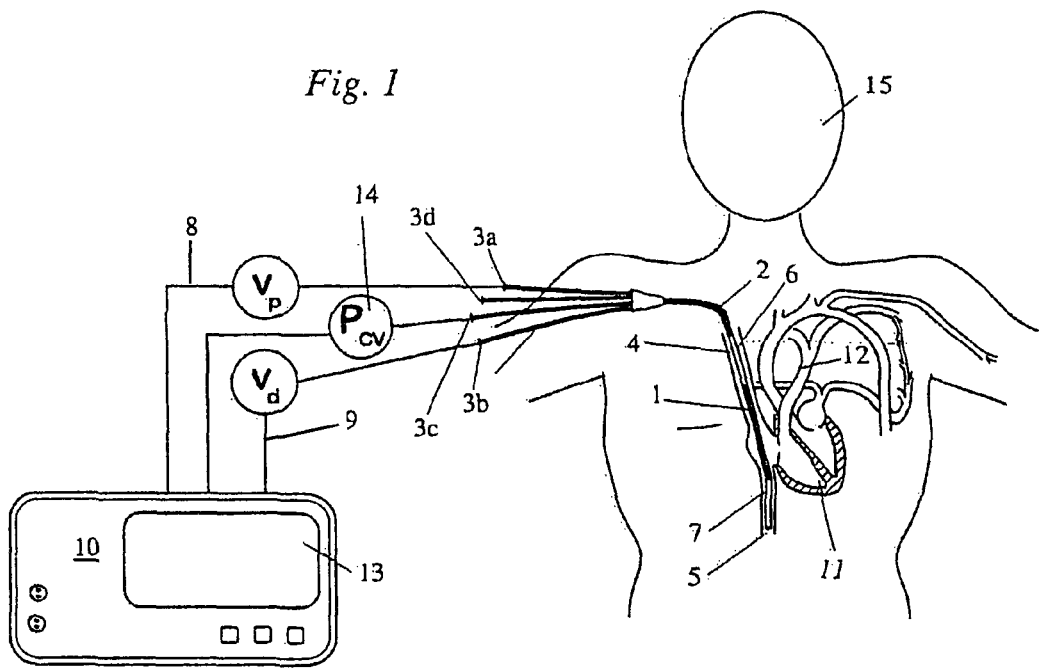
FIG. 1 shows a general measurement setup according to the present invention, wherein both flux measurement units are integrated in a central venous catheter.

In the drawings, corresponding features are marked with the same reference numerals where appropriate.

FIG. 1 shows a general measurement setup according to the present invention. The central venous sensor assembly 1 comprises a catheter body 2 with several proximal ports 3$a$, 3$b$, 3$c$, 3$d$. The catheter body 2 may, in particular with regard to materials used, be designed essentially like conventional central venous catheter bodies.

The intravascular part of the sensor assembly 1 extends from the vena cava superior 4 to the vena cava inferior 5 of the patient 15. The catheter portion placed in the vena cava superior 4 is equipped with a proximal flux measurement unit 6, and the catheter portion placed in the vena cava inferior 5 is equipped with a distal flux measurement unit 7.

A first input channel 8 supplies a measurement signal indicative of a flux vp to the evaluation unit 10 from which the latter calculates a blood flow in the vena cava superior. Likewise, a second input channel 9 supplies a measurement signal indicative of a flux vd to the evaluation unit 10 from which the latter calculates a blood flow rate in the vena cava inferior 5. Due to continuity, the sum of the flow rates in the upper and lower central veins 4, 5 corresponds to the flow rate in through the right heart 11 and in the pulmonary artery 12 and thus to cardiac output.

Thus determined cardiac output as well as other (optionally) determined parameters, such as those determined by methods other than using raw measurement data from a distal flux measurement unit and a proximal flux measurement unit, such as a calibration value representing a vessel diameter, and such as a calibration value representing a vessel cross sectional area, are displayed as numerical values and/or in charts and/or presented in graphical manner on the display 13 which may also serve for guiding operation. The evaluation unit 10 may alternatively calibrate cardiac output determination using at least one of those optionally determined parameters set forth above. The calibration values mentioned above may be determined by an estimation depending on other patient data such as size, weight, age and gender, or may be determined by a measurement. Advantageously, the display 13 can be configured as a touch screen to facilitate operation.

As an optional feature, the sensor assembly 1 comprises a pressure measurement lumen extending through the catheter body 2 and ending proximally at a dedicated proximal port 3$c$. A third input channel 14 is used to supply the pressure sensor signal indicative of central venous pressure Pcv to the evaluation unit 10. Central venous pressure Pcv and parameters derived therefrom may therefore be among the parameters displayed on display 13.

As another optional feature, the sensor assembly 1 comprises an additional lumen extending through the catheter body 2 and ending proximally at a dedicated proximal port 3$d$. The additional lumen may be used to inject substances or withdraw blood samples or to insert a fiber-optical probe or the like.

Figure 2:
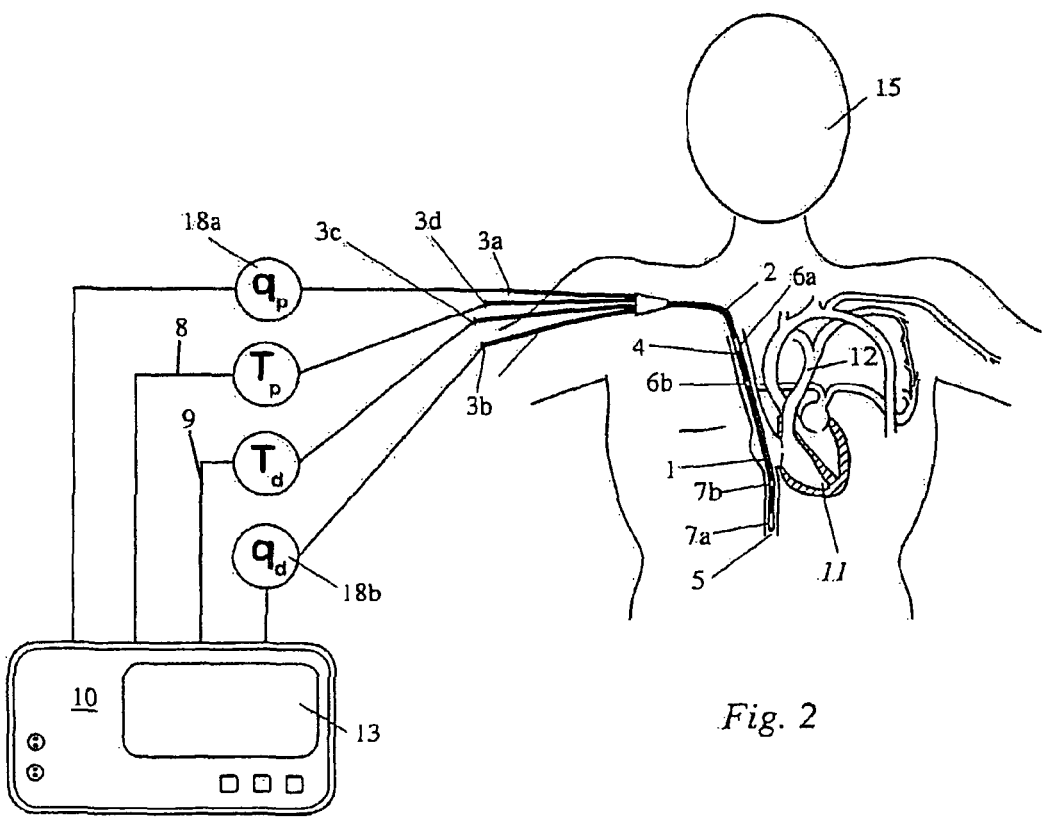
FIG. 2 shows a measurement setup with a catheter carrying two thermodilution flow measurement units.

FIG. 2 shows an advantageous embodiment of the present invention, wherein a distal heating element 7$a$ is arranged in the catheter portion placed in the vena cava inferior 5. A distal temperature sensor 7$b$ is arranged proximal to said distal heating element 7$a$ but still in the catheter portion placed in the vena cava inferior 5. Likewise, a proximal heating element 6a is arranged in the catheter portion placed in the vena cava superior 4. A proximal temperature sensor 6b is arranged distal to said proximal heating element 6a but still in the catheter portion placed in the vena cava superior 4. Thus, temperature sensors 6b, 7b are located downstream from respective heating elements 6a, 7a. As the temperature sensors 6b, 7b are used to detect travelling temperature deviations caused by heat pulses emitted from the respective heating elements 6a, 7a, and because, in order to measure a flux, some travelling distance needs to be interposed between creation of a travelling temperature deviation in the blood stream and detection thereof, the temperature sensors 6b, 7b must be spaced some distance apart from respective heating elements 6a, 7a.

The heating elements 6a, 7a may be designed like heating means known from the prior art, such as described in EP 1 236 435 A1. The heating elements are supplied with energy via respective power supply lines 18a, 18b. The evaluation unit 10 controls the supply of power qp, qd to the proximal and distal heating elements 6a, 7a respectively and records the timing thereof for evaluation purposes. The temperature response Tp, Td measured by the temperature sensors 6b, 7b is read in by the evaluation unit 10 via input channels 8 and 9, respectively. As both the distance between the respective heating element 6a, 7a and the respective temperature sensors 6b, 7b and the delay of the temperature response are known, a flux in both upper and lower central vein 4, 5 can be determined. Proper calibration, either by use of suitable empirical relations or by calibration measurements, will allow blood flow determination with high accuracy.

Figure 3:
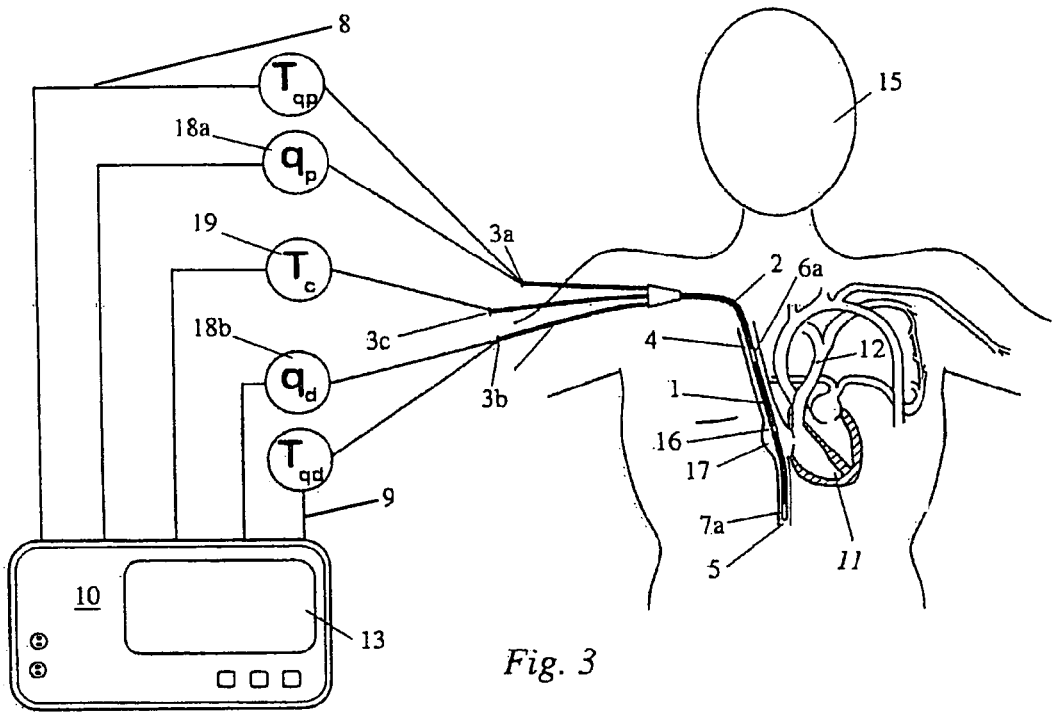
FIG. 3 shows a measurement setup with a catheter carrying two heat transfer flow measurement units.

FIG. 3 shows another advantageous embodiment of the present invention, wherein a distal heat transfer element 7a is arranged in the catheter portion placed in the vena cava inferior 5, and a proximal heat transfer element 6a is arranged in the catheter portion placed in the vena cava superior 4. A common temperature sensor 16 is arranged between said heat transfer elements 7a, 6a, e.g. in the right atrium 17, and spaced away some distance from both of the heat transfer elements 7a, 6a. The temperature sensor 16 may also be arranged proximal to said proximal heat transfer element 6a or distal to said distal heat transfer element 7a, i.e. upstream therefrom. The temperature signal of the temperature sensor 16 is read in by the evaluation unit 10 via the third input channel 19.

The heat transfer elements 7a, 6a are heated slightly above the blood temperature Tc determined by the temperature sensor 16. Therein, the heat transfer elements are supplied with energy via respective power supply lines 18a, 18b. The evaluation unit 10 controls the supply of power qp, qd to the proximal and distal heat transfer elements 6a, 7a respectively and registers the power supplied over time for evaluation purposes.

The respective temperatures Tqp, Tqd of the heat transfer elements 7a, 6a are measured by respective temperature sensors the signals of which are read in by the evaluation unit 10 via the first and second input channel 8, 9 respectively.

The respective blood flow rate in the upper and lower central vein 4, 5 may be calculated using algorithms known per se from the prior art in connection with determining blood flow rate in the pulmonary artery (based on the principle of employing a heat transfer element).

The sum of the blood flow rates in the upper and lower central vein 4, 5, at least if averaged over time, can be considered equal with the blood flow rate through the right heart 11 and thus with cardiac output.

The heat transfer elements 7a, 6a may be designed like heat transfer elements known from the prior art, e.g. as described in WO 01/13808 A1.

Figure 4:
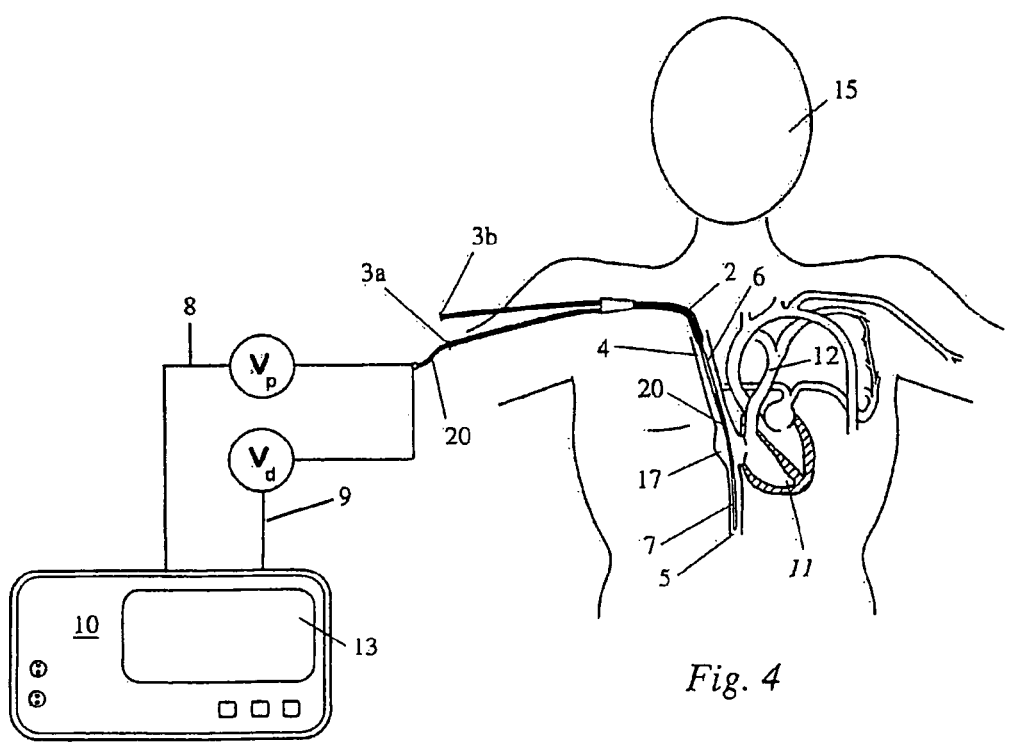
FIG. 4 shows a general measurement setup similar to FIG. 1, wherein, however, both flux measurement units are integrated in a central venous probe inserted through a short catheter.

FIG. 4 shows a general measurement setup similar to FIG. 1. However, a shorter catheter body 2 is provided, which comprises a probe lumen proximally terminating in catheter port 3a, through which the sensor probe 20 is inserted.

The intravascular part of the sensor probe 20 extends from the vena cava superior 4 to the vena cava inferior 5 of the patient 15. The proximal probe portion placed in the vena cava superior 4 is equipped with the proximal flux measurement unit 6, and the distal probe portion placed in the vena cava inferior 5 is equipped with a distal flux measurement unit 7.

A first input channel 8 supplies a measurement signal indicative of a flux vp to the evaluation unit 10 from which the latter calculates a blood flow in the vena cava superior. Likewise, a second input channel 9 supplies a measurement signal indicative of a flux vd to the evaluation unit 10 from which the latter calculates a blood flow rate in the vena cava inferior 5. Due to continuity, the sum of the flow rates in the upper and lower central veins 4, 5 corresponds to the flow rate through the right heart 11 and in the pulmonary artery 12 and thus to cardiac output.

Thus determined cardiac output as well as other (optionally) determined parameters are displayed as numerical values and/or in charts and/or presented in graphical manner on the display 13 which may also serve to guide operation. Advantageously, the display 13 can be configured as a touch screen to facilitate operation.

As an optional feature, the catheter comprises an additional lumen extending through the catheter body 2 and ending proximally at a dedicated proximal port 3b. The additional lumen may be used, e.g., to inject substances or withdraw blood samples.

Figure 5:
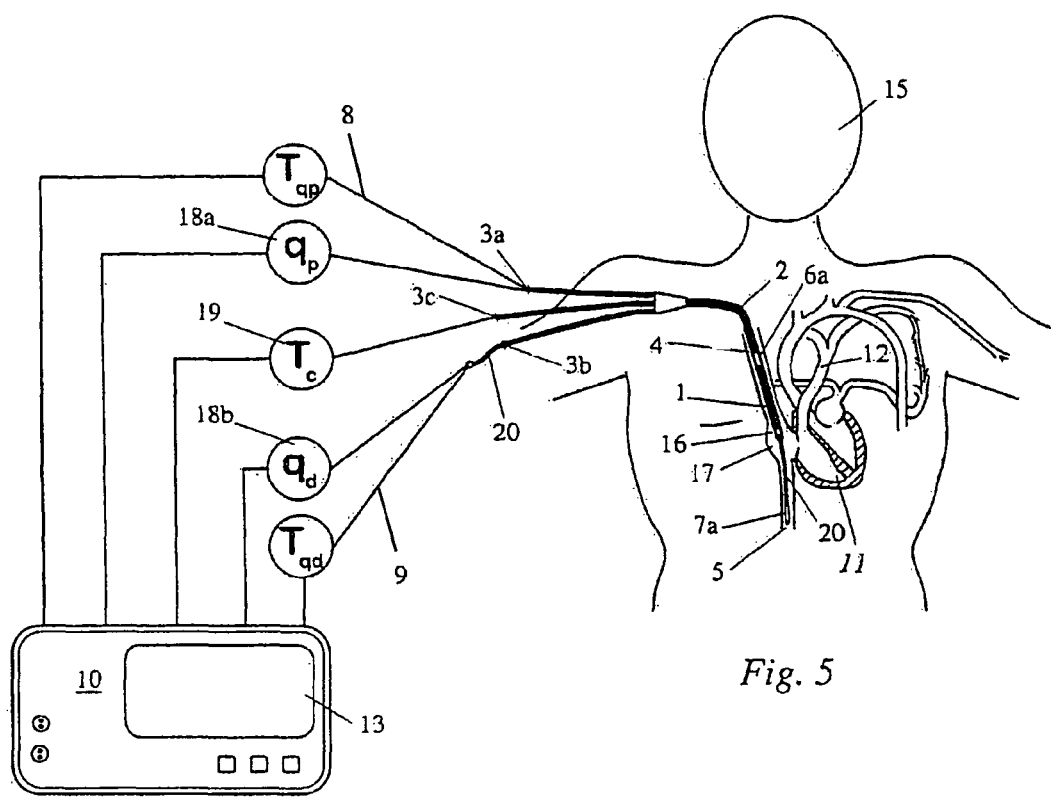
FIG. 5 shows a measurement setup with two heat transfer flow measurement units similar to FIG. 3, wherein, however, only the proximal heat transfer element is integrated in a central venous catheter whereas the distal heat transfer element is integrated in a central venous probe inserted through the catheter.

FIG. 5 shows a setup similar to FIG. 3. However, a shorter catheter body 2 is provided, which does not extend into the vena cava inferior 5, and which comprises a probe lumen proximally terminating in catheter port 3b, through which the sensor probe 20 is inserted.

The distal heat transfer element 7a is arranged in the intravascular probe portion placed in the vena cava inferior 5, and the proximal heat transfer element 6a is arranged in the intravascular catheter portion placed in the vena cava superior 4. A common temperature sensor 16 is arranged at or close to the distal end of the catheter body 2 and is thus placed between said heat transfer elements 7a, 6a, e.g. in the right atrium 17, and spaced away some distance from both of the heat transfer elements 7a, 6a. The temperature signal of the temperature sensor 16 is read in by the evaluation unit 10 via the third input channel 19.

The heat transfer elements 7a, 6a are heated slightly above the blood temperature Tc determined by the temperature sensor 16. Therein, the heat transfer elements are supplied with energy via respective power supply lines 18a, 18b. The evaluation unit 10 controls the supply of power qp, qd to the proximal and distal heat transfer elements 6a, 7a respectively and registers the power supplied over time for evaluation purposes.

The respective temperatures Tqp, Tqd of the heat transfer elements 7a, 6a are measured by respective temperature sensors the signals of which are read in by the evaluation unit 10 via the first and second input channel 8, 9 respectively.

The respective blood flow rate in the upper and lower central vein 4, 5 may be calculated using algorithms known per se from the prior art in connection with determining blood flow rate in the pulmonary artery (based on the principle of employing a heat transfer element).

The sum of the blood flow rates in the upper and lower central vein 4, 5, at least if averaged over time, can be considered equal with the blood flow rate through the right heart 11 and thus with cardiac output.

The heat transfer elements 7a, 6a may be designed similar as heat transfer elements known from the prior art, e.g. as described in WO 01/13808 A1.

The invention claimed is:

1. A central venous sensor assembly for measuring physiological data for cardiac output determination, said measurement assembly comprising:
   a distal intravascular portion for placement in the vena cava inferior of a patient and a proximal intravascular portion for placement in the vena cava superior of the patient,
   a distal flux measurement unit arranged in the distal intravascular portion and adapted to provide raw measurement data for determination of a blood flow in the direction towards the proximal intravascular portion, and
   a proximal flux measurement unit arranged in the proximal intravascular portion and adapted to provide raw measurement data for determination of a blood flow in the direction towards the distal intravascular portion,
   wherein the venous sensor assembly is connected to an evaluation unit comprising a first input channel for receiving raw measurement data from said distal flux measurement unit and a second input channel for receiving raw measurement data from said proximal flux measurement unit and being adapted to:
   determine a first blood flow from the raw measurement data received from said distal flux measurement unit,
   determine a second blood flow from the raw measurement data received from said proximal flux measurement unit, and
   determine said cardiac output as a sum of said first blood flow and said second blood flow.

2. The central venous sensor assembly according to claim 1, wherein at least one of said flux measurement units comprises a heat transfer device for determining an amount of energy needed per unit time to maintain a given temperature of the heat transfer device.

3. The central venous sensor assembly according to claim 1, wherein said distal flux measurement unit comprises:
   a distal temperature influencing element for influencing the temperature of blood passing said distal temperature influencing element, and
   a distal temperature sensor, said distal temperature sensor being arranged in a position proximal with respect to said distal temperature influencing element.

4. The central venous sensor assembly according to claim 3, wherein said distal temperature influencing element is a heating element.

5. The central venous sensor assembly according to claim 3, wherein said distal temperature influencing element is a cooling element.

6. The central venous sensor assembly according to claim 1, wherein said proximal flux measurement unit comprises:
   a proximal temperature influencing element for influencing the temperature of blood passing said proximal temperature influencing element, and
   a proximal temperature sensor, said proximal temperature sensor being arranged in a position distal with respect to said proximal temperature influencing element.

7. The central venous sensor assembly according to claim 6, wherein said proximal temperature influencing element is a cooling element.

8. The central venous sensor assembly according to claim 6, wherein said proximal temperature influencing element is a heating element.

9. The central venous sensor assembly according to claim 1, said sensor assembly including a probe comprising a distal probe portion for placement in the vena cava inferior of the patient and a proximal probe portion for placement in the vena cava superior of the patient, wherein said distal flux measurement unit is arranged in the distal probe portion and said proximal flux measurement unit is arranged in the proximal probe portion.

10. The central venous sensor assembly according to claim 9, which further comprises a catheter through which said probe can be inserted to be placed in the vena cava superior and vena cava inferior of said patient.

11. The central venous sensor assembly according to claim 10, wherein said catheter comprises a pressure measurement lumen.

12. The central venous sensor assembly according to claim 1, said sensor assembly including:
   a central venous catheter comprising an elongated catheter body for placement in the vena cava superior of a patient and a probe lumen, and
   a probe adapted for being inserted through said probe lumen, said probe having a distal probe portion for placement in the vena cava inferior of the patient,
   wherein said distal flux measurement unit is arranged in the distal probe portion and said proximal flux measurement unit is integrated in the catheter body.

13. The central venous sensor assembly according to claim 12, wherein said catheter comprises a pressure measurement lumen.

14. The central venous sensor assembly according to claim 1, said sensor assembly including a central venous catheter having an elongated catheter body with a distal body portion for placement in the vena cava inferior of a patient and a proximal body portion for placement in the vena cava superior of the patient,
   wherein said distal flux measurement unit is arranged in the distal body portion and said proximal flux measurement unit is arranged in the proximal body portion.

15. The central venous sensor assembly according to claim 14, wherein said catheter comprises a pressure measurement lumen.

16. The central venous sensor assembly according to claim 1, wherein said evaluation unit is further adapted to calibrate cardiac output determination using at least one of:
   a reference cardiac output determined by a method other then using said raw measurement data from said distal flux measurement unit and said proximal flux measurement unit,
   a calibration value representing a vessel diameter, and
   a calibration value representing a vessel cross sectional area.

17. The central venous sensor assembly according to claim 16, wherein said evaluation unit is further adapted to calibrate cardiac output determination using at least one of:
   a calibration value representing a vessel diameter, and
   a calibration value representing a vessel cross sectional area, and
   wherein at least one of said calibration value representing a vessel diameter or said calibration value representing a vessel cross sectional area is determined by an estimation depending on other patient data, such as size, weight, age and gender.

18. The central venous sensor assembly according to claim 16, wherein said evaluation unit is further adapted to calibrate cardiac output determination using at least one of:
- a calibration value representing a vessel diameter, and
- a calibration value representing a vessel cross sectional area, and
- wherein at least one of said calibration value representing a vessel diameter or said calibration value representing a vessel cross sectional area is determined by measurement.

19. A method for determining cardiac output of a patient comprising the steps of:
- receiving raw measurement data from a first flux measurement unit which measures flux-related raw measurement data in the vena cava inferior,
- receiving raw measurement data from a second flux measurement unit which measures flux-related raw measurement data in the vena cava superior,
- determining a first blood flow from the raw measurement data received from said first flux measurement unit,
- determining a second blood flow from the raw measurement data received from said second flux measurement unit, and
- determining said cardiac output as a sum of said first blood flow and said second blood flow.

20. The method according to claim 19, wherein cardiac output determination is calibrated using at least one of:
- a reference cardiac output determined by a method other then using said raw measurement data from said first flux measurement unit and said second flux measurement unit,
- a calibration value representing a vessel diameter, and
- a calibration value representing a vessel cross sectional area.

21. The method according to claim 20, wherein cardiac output determination is calibrated using at least one of:
- a calibration value representing a vessel diameter, and
- a calibration value representing a vessel cross sectional area,
- wherein at least one of said calibration value representing a vessel diameter and said calibration value representing a vessel cross sectional area is determined by performing an estimation depending on other patient data, such as size, weight, age and gender.

22. The method according to claim 20, wherein cardiac output determination is calibrated using at least one of:
- a calibration value representing a vessel diameter, and
- a calibration value representing a vessel cross sectional area,
- wherein at least one of said calibration value representing a vessel diameter or said calibration value representing a vessel cross sectional area is determined by measurement.

* * * * *